US007989214B2

(12) United States Patent
Bianchessi et al.

(10) Patent No.: US 7,989,214 B2
(45) Date of Patent: Aug. 2, 2011

(54) SELF-SEALING MICROREACTOR AND METHOD FOR CARRYING OUT A REACTION

(75) Inventors: Marco Angelo Bianchessi, Melzo (IT); Alessandro Cocci, Rovellasca (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 0 days.

(21) Appl. No.: 12/647,748

(22) Filed: Dec. 28, 2009

(65) Prior Publication Data

US 2010/0167414 A1 Jul. 1, 2010

(30) Foreign Application Priority Data

Dec. 29, 2008 (IT) .............................. TO2008A1001

(51) Int. Cl.
*G01N 1/00* (2006.01)
*G01N 33/50* (2006.01)
*C12M 1/18* (2006.01)

(52) U.S. Cl. ........ 436/174; 422/551; 422/552; 422/553; 435/287.2; 435/288.4; 436/86; 436/94; 436/181; 436/183

(58) Field of Classification Search .................. 422/102, 422/551–553; 435/287.2, 288.4; 436/86, 436/94, 174, 181, 183
See application file for complete search history.

(56) References Cited

U.S. PATENT DOCUMENTS 3,798,772 A * 3/1974 Eberhard ........................ 433/74
4,053,362 A * 10/1977 Sforza ........................... 435/243
4,066,116 A * 1/1978 Blazek et al. ................... 164/17
5,282,543 A * 2/1994 Picozza et al. ................ 220/255
5,411,876 A * 5/1995 Bloch et al. .................. 435/91.2
5,475,610 A * 12/1995 Atwood et al. ............... 700/269
5,487,972 A * 1/1996 Gelfand et al. .................... 435/6
5,538,871 A * 7/1996 Nuovo et al. ................ 435/91.2
5,565,339 A * 10/1996 Bloch et al. .................. 435/91.2
5,576,197 A 11/1996 Arnold
5,599,660 A * 2/1997 Ramanujam et al. ............. 435/4
5,643,764 A * 7/1997 Kosak et al. ................. 435/91.1
5,968,729 A 10/1999 Kosak et al.
6,074,868 A * 6/2000 Blumenfeld ............... 435/286.1
6,110,665 A * 8/2000 Fenger et al. ...................... 435/6
6,300,124 B1 * 10/2001 Blumenfeld et al. ...... 435/287.2
6,322,988 B1 * 11/2001 Dawson et al. ................... 435/6
6,720,149 B1 * 4/2004 Rava et al. ......................... 506/4
7,341,865 B1 * 3/2008 Norris et al. ............... 435/287.2
2002/0072112 A1 * 6/2002 Atwood et al. ............ 435/303.1
2004/0219732 A1 11/2004 Burns et al.
2007/0053800 A1 * 3/2007 Lehto ............................ 422/102
2009/0226911 A1 * 9/2009 Mauk et al. ........................ 435/6

FOREIGN PATENT DOCUMENTS

JP 2007090290 4/2007

* cited by examiner

*Primary Examiner* — Arlen Soderquist
(74) *Attorney, Agent, or Firm* — Boulware & Valoir

(57) ABSTRACT

A microreactor includes a shell structure (2, 3), having a bottom wall (2) and a peripheral wall (3); a layer (5), accommodated in the shell structure (2, 3) and having cavities (9, 10) formed therein, the cavities being accessible form outside the shell structure (2, 3); reagents (17), arranged between the bottom wall (2) and the layer (5), at locations corresponding to the cavities (9, 10). The layer (5) is made of a meltable material that is solid at room temperature, has a melting point ($T_{MP}$) lower than a maximum operative temperature ($T_{MAX}$) required by reactions performable through the microreactor (1) and is not miscible with water. The melting point ($T_{MP}$) may be between 50° C. and 70° C. In one embodiment, the melting point ($T_{MP}$) is lower than a minimum operative temperature ($T_{MIN}$) required by reactions performable through the microreactor (1).

18 Claims, 5 Drawing Sheets

SELF-SEALING MICROREACTOR AND METHOD FOR CARRYING OUT A REACTION

CROSS-REFERENCE TO RELATED APPLICATIONS

This application claims priority to Italian Application No. TO2008A001001 filed on Dec. 29, 2008, incorporated herein by reference in its entirety.

FEDERALLY SPONSORED RESEARCH STATEMENT

Not applicable.

REFERENCE TO MICROFICHE APPENDIX

Not applicable.

FIELD OF THE INVENTION

The present invention relates to a self-sealing microreactor and to a method for carrying out a reaction.

BACKGROUND OF THE INVENTION

Lab-On-Chip (LoC) systems are designed to carry out one or more steps of a chemical or biological process, often in a disposable sample cartridge or a silicon chip that is controlled and read by a reusable, portable device. For example, LoC systems are widely used to perform analyses such as PCR amplification, antibody testing, biochemical reactions, and microarray-based DNA, RNA, or protein analyses.

Lab-On-Chip systems are proving to be effective in a wide range of practical situations and provide several advantages over conventional bench top methodologies. For example, LoC systems allow completely automated and repeatable processes, minimize sample size, ensure accurate control of process parameters, especially temperature, and the single use sample cartridges minimize contamination and provide for convenient disposal. Moreover, the LoC cartridges and the device that controls the process parameters and reads the results are portable. Thus, analyses can be carried out in the field, immediately after sample collection, and problems of sample preservation are eliminated and results are obtained much more quickly.

However, certain issues related to use of LoC systems still need to be satisfactorily addressed—in particular, fluid loss due to evaporation. Samples processed in LoC systems are usually water based, and thermal cycles raise the temperature and favor evaporation. Since the volumes involved in LoC reactions are typically very small, evaporation can easily affect the concentration of reagents and alter results.

LoC inlets can be sealed by applying a rigid cap once the chip or cartridge has been filled with sample. This solution is not optimal, however, because pressure dramatically increases on heating, possibly affecting the reaction or breaking the cap or even the entire chip.

Integrated membrane valves or bonded elastic caps can cope with pressure increases, but manufacturing and use of LoC cartridges that incorporate such solutions are more complex and costly.

An alternative solution, used historically in bench top PCR reactions, requires the addition of a mineral oil layer on top of the sample. Mineral oil has a lower density than water, forms a film on the surface of the sample and prevents its evaporation. At the same time, the thin film allows expansion of the sample caused by thermal cycling, so that pressure is sufficiently stable to preserve both the reaction conditions and chip integrity.

However, addition of mineral oil must be carried out manually after loading the sample into the chip, and the risk of sample contamination is considerable and preferably avoided. Also, since there is no proper cap, the sample may spill during movement, exposing laboratory technicians and the laboratory site to dangerous pathogens or toxic reagents.

The object of this invention, therefore, is to provide a self-sealing microreactor and a method for carrying out a reaction that is free from the above described limitations.

SUMMARY OF THE INVENTION

The present invention provides a microreactor for performing chemical or biochemical reactions and a method for performing those reactions. Generally speaking the self-sealing reactor of the invention employs a meltable portion to seal the chamber. The meltable portion also has cavities for receiving a sample for analysis. Thus, during use, the meltable portion completely or partially melts, allowing thermal expansion inside the reactor. However, the melted material is immiscible with the sample, thus preventing mixing with the sample during the high temperature phase of a reaction. After use, the melted material re-solidifies, preventing contamination and re-sealing the chamber for ease of transport and use.

BRIEF DESCRIPTION OF THE DRAWINGS

For the understanding of the present invention, some embodiments thereof will be now described, purely as non-limitative examples, with reference to the enclosed drawings, wherein.

DETAILED DESCRIPTION OF THE INVENTION

Figure 1:
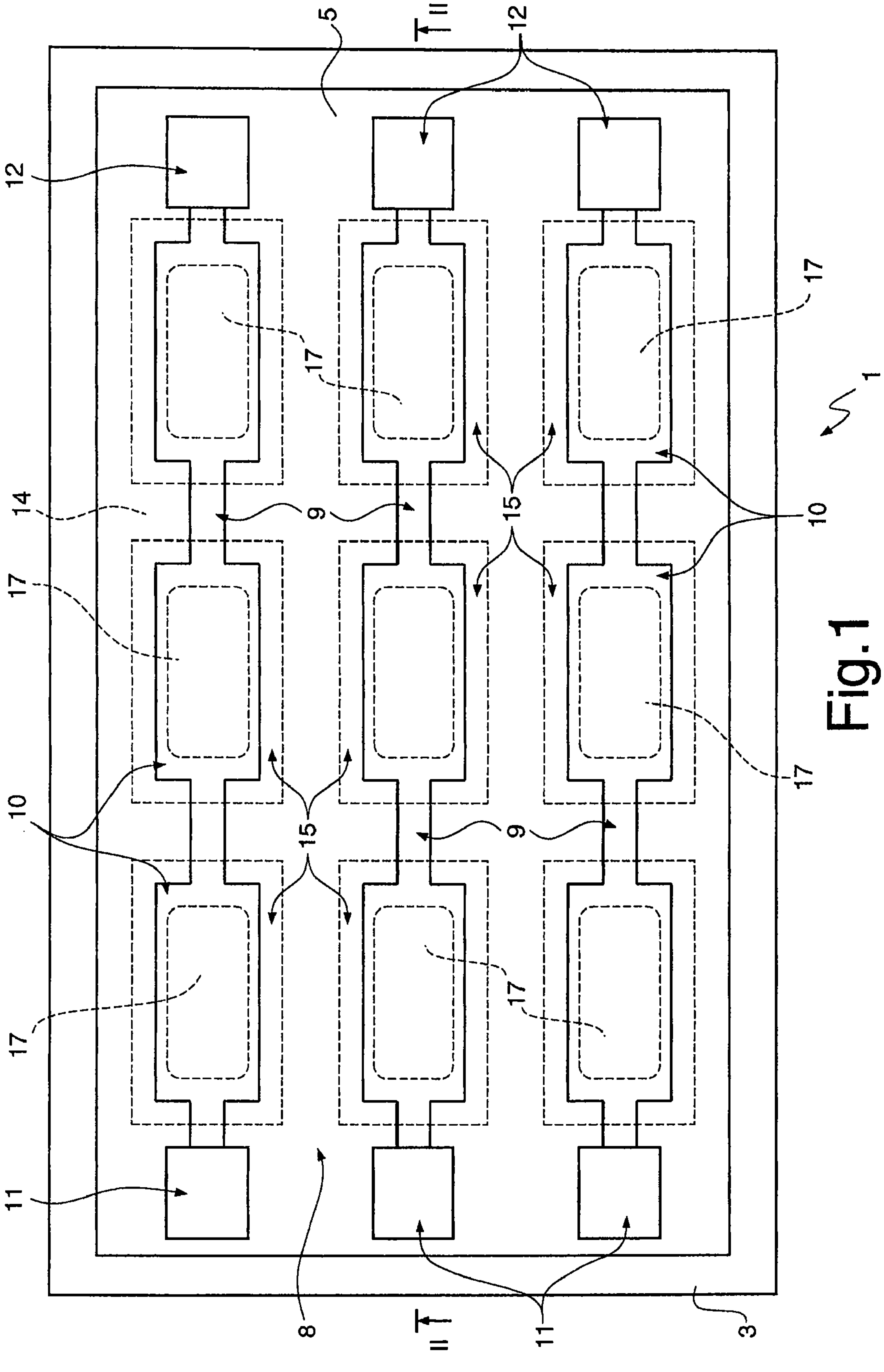
FIG. 1 is a top plan view of a microreactor according to one embodiment of the present invention.
Figure 2:
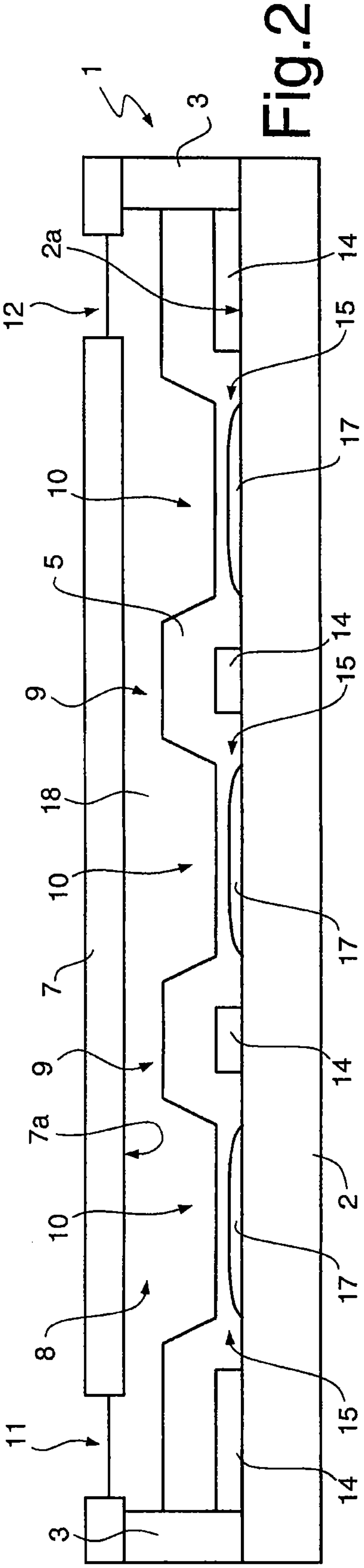
FIG. 2 is a cross-section through the microreactor of FIG. 1, taken along line II-II of FIG. 1, in an initial operating configuration.

FIGS. 1 and 2 show a microreactor, namely for Lab-on-Chip applications, as a whole designated by the reference number 1. The microreactor 1 comprises a substrate 2 (seen in FIG. 2), a frame 3, a meltable layer 5 and a cap plate 7 (not shown in FIG. 1 for clarity).

The substrate 2 may be made of a variety of materials, such as a semiconductor material, glass, ceramic, or plastic or other resin. In one embodiment, for example, the substrate 2 is of monocrystalline silicon.

The frame 3 is bonded to the substrate 2 along an outer perimeter thereof, thus forming a shell structure having a bottom surface (the substrate 2) and a peripheral or side wall (the frame 3). Alternatively, the frame 3 may be integral with the substrate 2, for example by etching or by deposition of an edge as needed on the substrate.

The shell structure is closed by the cap plate 7, that is bonded, welded, glued or otherwise attached to the frame 3. In one embodiment, the frame 3 and the cap plate 7 are made of plastic, but it is understood that other material may be used, such as a semiconductor material or glass. Moreover, different materials may be used for the frame 3 and the cap plate 7.

In one embodiment, an internal surface 7*a* of the cap plate 7 is treated to be made hydrophobic or treated to attract a meltable material, described below.

The meltable layer 5 is accommodated inside the frame 3, that serves, together with the substrate 2 and cap plate 7, as a containment structure.

Figure 3:
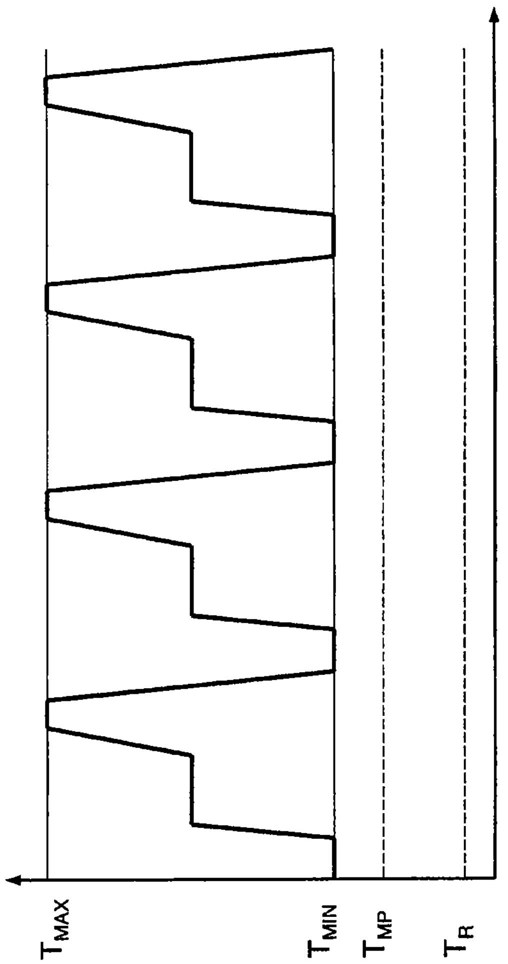
FIG. 3 is a graph showing a typical temperature profile of the microreactor of FIG. 1 during temperature cycling.

The meltable layer 5 is made of a meltable material that is solid at a room temperature $T_R$ (about 25° C.), but has a melting point $T_{MP}$ below a maximum operative temperature $T_{MAX}$ (of the microreactor 1 (see also FIG. 3). In the embodiment herein described, moreover, the melting point $T_{MP}$ is around or lower than a minimum operative temperature $T_{MIN}$ of the microreactor 1. More precisely, the microreactor 1, as virtually all microreactors, is designed for a specific process (e.g. DNA amplification), that requires iteratively heating and cooling the reagents between a number of operative temperatures according to a process thermal cycle. The maximum operative temperature $T_{MAX}$ and the minimum operative temperature $T_{MIN}$ are respectively the maximum temperature and the minimum temperature reached during each thermal cycle of the microreactor 1. Of course, different microreactors may be designed to carry out different processes, which may involve different thermal cycles and operative maximum temperatures. For example, the melting point $T_{MP}$ is in the range of 50° C. to 70° C. In any case, the melting point $T_{MP}$ is such that the fluidic layer 5 melts when the microreactor 1 is operated to carry out the intended process. If the meltable layer material is selected to have the melting point $T_{MP}$ lower than the minimum operative temperature $T_{MIN}$, the meltable layer material is always liquid when the microreactor 1 is operated.

Thus, in use the meltable layer melts, and allows expansion with temperature and prevents increases in pressure from damaging the chip or interfering with the reaction. However, after use, the layer re-solidifies, providing an adequate seal against contamination and spillage.

The meltable layer material forming the meltable layer 5 is immiscible with water and, in one embodiment, has affinity with hydrophobic materials, in particular with the material on the surface 7*a* of the cap plate 7. In another embodiment, however, the meltable layer material is hydrophilic (e.g. a hydrophilic gel) and is therefore immiscible with hydrophobic samples. In one embodiment, the density of the meltable layer 5 is lower than the density of water, so that the melted material floats on water. The hydrophobicity of the material and the surface 7*a* can of course be reversed when assaying lipid and other hydrophobic samples. Further, the placement and exact shape of the meltable layer can vary widely, provided only that the melted layer functions (by a combination of surface tension, and/or attractive and repulsive forces of the hydrophobic and hydrophilic areas) to seal the device when in use.

In one embodiment, the meltable layer comprises wax and/or paraffin. Other examples of suitable materials solid greases, such as cocoa butter, and gels such as hydrogels or organogels.

The meltable layer 5 defines one side of a microfluidic circuit 8, that includes channels 9 and chambers 10 and is upwardly delimited by the cap plate 7. Preferably, the cap plate 7 has flat surfaces, whereas the channels 9 and the chambers 10 are formed in the meltable layer 5. Inlets 11 and outlets 12 made through the cap plate 7 provide access to the microfluidic circuit 8 from the outside. Any arrangement of microfluidic circuit can be used, depending on the needs of the reaction.

In one embodiment, a confining structure 14 is formed on a surface 2*a* of the substrate 2, on which the meltable layer 5 is arranged and serves to attract the meltable material and may also act as a space filler. The confining structure 14 is therefore set between the substrate 2 and the meltable layer 5. The confining structure 14 comprises stripes of e.g., a hydrophobic material (e.g. SU8, dry resist, silane, teflon, polypropylene) that define windows 15 (or "gap" in the hydrophobic material) around the chambers 10 of the microfluidic circuit 8.

The surface 2*a* of the substrate 2 is also treated to be made hydrophilic at least within the windows 15. For example, the surface 2*a* may be coated with plasma activated SiO2, BSA (Bovine Serum Albumin), PEG (Polyethylene Glycol).

The hydrophilic coating attracts the aqueous sample, and the hydrophobic coating attracts the melted material, and thus the coatings serve to direct and contain the sample and seal the microreactor with the meltable layer 5. As mentioned above, the hydrophobicity can be reversed for a lipid-based reaction.

Spots of reagents 17 are deposited on the substrate 2 in the windows 15 and are encapsulated between the substrate 2 and the meltable layer 5, below respective chambers 10. Different reagents 17 may be used at respective chambers 10, in order to perform different reactions simultaneously.

The microreactor 1 may be made by forming first the confining structure 14 on the substrate 2 by deposition and/or etching. After bonding the frame 3 to the substrate 2, reagents 17 are deposited in the windows 15 in the form of dry or frozen powder or gel. In one embodiment, the frame 3 may be bonded after depositing the reagents 17. Then, the meltable layer 5 is deposited on the substrate 2, covering the confining structure 14 and the reagents 17. The meltable material can be deposited in a pattern so as to form channels 9 and channels 10, or can be embossed, molded or etched to create channels 9 and chambers 10 of the microfluidic circuit 8. At the end, the cap plate 7 is bonded to the frame 3.

Figure 4:
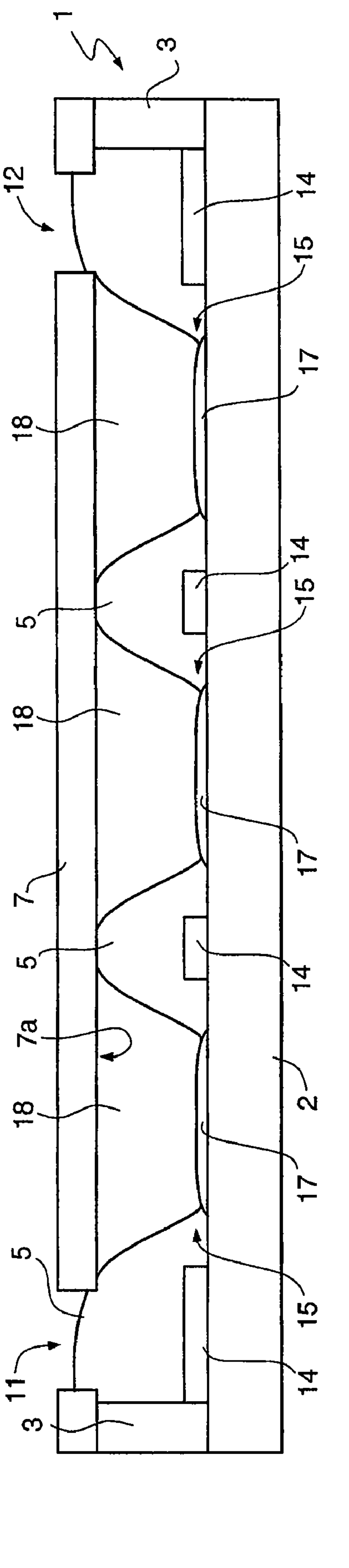
FIG. 4 shows the cross-section of FIG. 2 in an intermediate operative configuration.
Figure 5:
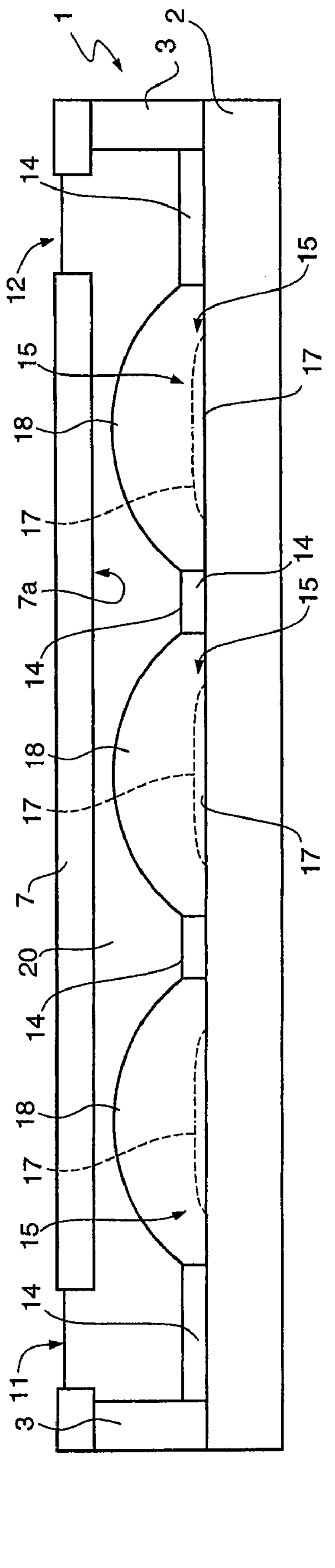
FIG. 5 shows the cross-section of FIG. 2 in a final operative configuration.

To carry out chemical processes by the microreactor 1, a fluid sample 18 to be processed is first loaded into the microfluidic circuit 8, which is thus filled (FIG. 2). The microreactor 1 is then heated over the melting point $T_{MP}$ of the meltable layer material forming the meltable layer 5 (FIG. 4). Molten meltable layer material tends to reach the surface 7*a* of the cap plate 7 due to affinity, and leaves the substrate 2 free in the windows 15. Moreover, the sample 18, which is a water-based solution in this example, moves away from the cap plate 7, which is hydrophobic, and approaches the free surface 2*a* of the substrate 2 in the windows 15, which is hydrophilic. The liquid material and the sample 18 are immiscible and remain separated. Due to the shape of the confining structure 14 and to surface tension or cohesion forces, the sample 18 forms nearly spherical drops in respective windows 15 and mixes with the reagents 17 stored therein (FIG. 5). The volume and exact shape of the droplets are determined by the volume of corresponding chambers 10 and by the surface tension at the interface between the sample 18 and the meltable layer material, that may be accurately determined and is already known for most materials.

After melting, the meltable layer material forms a seal film 20 that closes inlets 11 and outlets 12 and prevents evaporation of the sample 18. Thus, the microreactor 1 is self-sealing during operation. In this condition, the seal film 20 functions like a mineral oil seal and accommodates pressure variations caused by thermal cycling. No mechanical stress is thus generated and risk of failure or fluid loss is eliminated.

When the process is terminated, the seal film 20 again solidifies, so that the drops of samples are trapped inside the microreactor 1 and cannot escape through inlets 11 and outlets 12. Thus, sample contamination is prevented during and after the process. Moreover infectious or toxic substances that may be possibly contained in the sample or in the reagents cannot contaminate the environment when the microreactor 1 is disposed of.

Moreover, the drops of the sample 18 accommodated in the windows 15 form lenses that may be exploited to improve optical inspection of processed substances. To this end, also the cap plate 7 may be made of a transparent material, such as glass or optically clear plastic.

Calibration of the device 1 is also facilitated. Resistors used as temperature sensors are affected by manufacturing processes and it may be necessary to determine at least two reference points, in which both temperature and resistance values are known, to perform reliable calibration of the cartridge. A first reference point may be easily determined by simultaneously measuring ambient temperature and rest resistance value. A second reference point may be determined at the melting temperature of the seal layer material. Due to fusion latent heat, in fact, temperature is stable when the seal layer material melts and is known from the composition thereof. Thus, when the device 1 is heated temperature detected by the sensor rises until the melting temperature and then remains constant for a period (plateau). Thus, the second point can be determined by measuring the resistance value during the plateau.

In other embodiments, the microreactor may selectively exploit either hydrophobic properties of the cap plate and affinity of the meltable layer material with hydrophobic materials, or a meltable layer material with lower specific weight than water. In the latter case, the microreactor needs to rest on a nearly horizontal plane during operation.

In one embodiment, the confining structure 14 is not provided, as it is optional and serves merely to reduce the amount of meltable layer material needed and to raise it towards the opposite surface, helping to seal the device during use.

Figure 6:
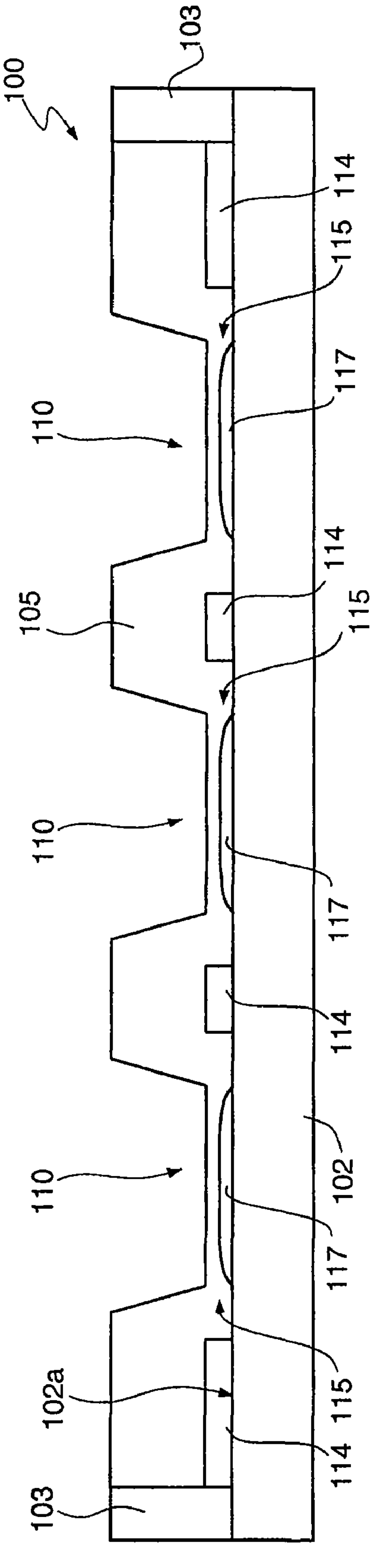
FIG. 6 is a cross-section through a microreactor according to another embodiment of the present invention, in an initial operating configuration.

According to another embodiment, illustrated in FIG. 6, a microreactor 100 comprises a substrate 102, a frame 103, bonded to the substrate 102, and a meltable layer 105, accommodated inside the frame 103.

The frame 103 and the substrate 102 form a shell structure having a bottom wall (the substrate 102) and a peripheral wall (the frame 103). No cap is needed.

Wells 110 are formed in the meltable layer 105 and are directly accessible from outside for receiving a sample to be processed. The sample may be dispensed e.g. through micropipettes.

The meltable layer 105 is made of a meltable layer material that is solid at a room temperature $T_R$ and has a melting point $T_{MP}$ at or lower than a minimum operative temperature $T_{MIN}$ of the microreactor 100.

Moreover, the meltable layer material forming the meltable layer 105 is not miscible with the sample. The density of the meltable layer material 105 is lower than the density of the sample, so that molten meltable layer material floats. The meltable layer material may contain paraffin.

A confining structure 114 may be formed on a surface 102*a* of the substrate 102, between the substrate 102 and the meltable layer 105. The confining structure 114 comprises stripes of hydrophobic material (e.g. SU8, dry resist, silane, teflon, polypropylene) that defines windows 115 around the wells 110.

The surface 102*a* is also treated to be made hydrophilic at least within the windows 115. For example, the surface 2*a* may be coated with plasma activated SiO2, BSA (Bovine Serum Albumin), or PEG (Polyethylene Glycol).

Spots of reagents 117 are deposited on the substrate 102 in the windows 115 and are encapsulated between the substrate 102 and the meltable layer 105, below respective wells 110. Different reagents 117 may be used at respective wells 110, in order to perform different reactions simultaneously.

Figure 7:
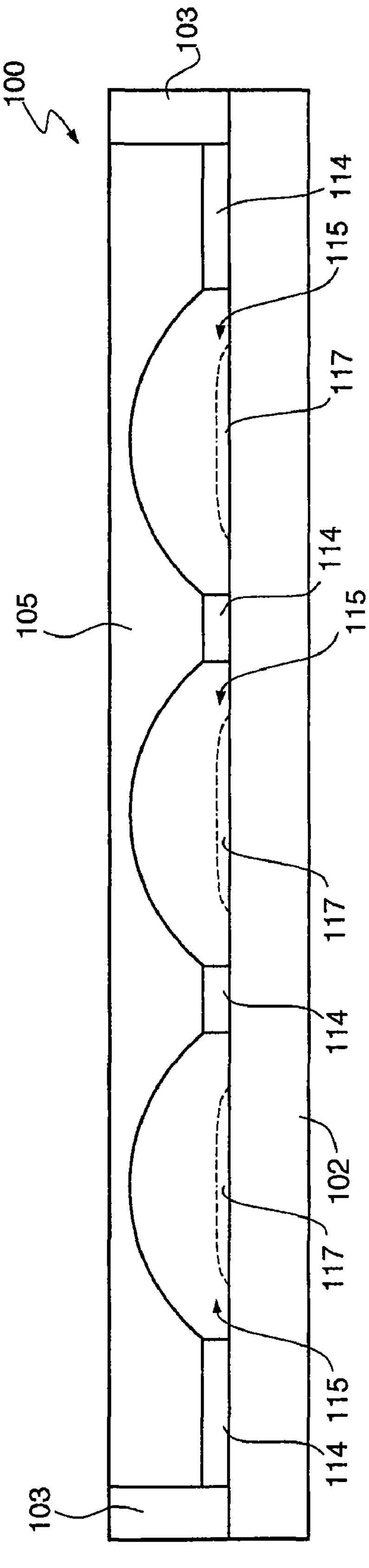
FIG. 7 shows the cross-section of FIG. 6 in a final operative configuration.

FIG. 7 shows the microreactor 100 after processing, where the meltable layer forms a seal that hardens on completion of the reaction.

Figure 8:
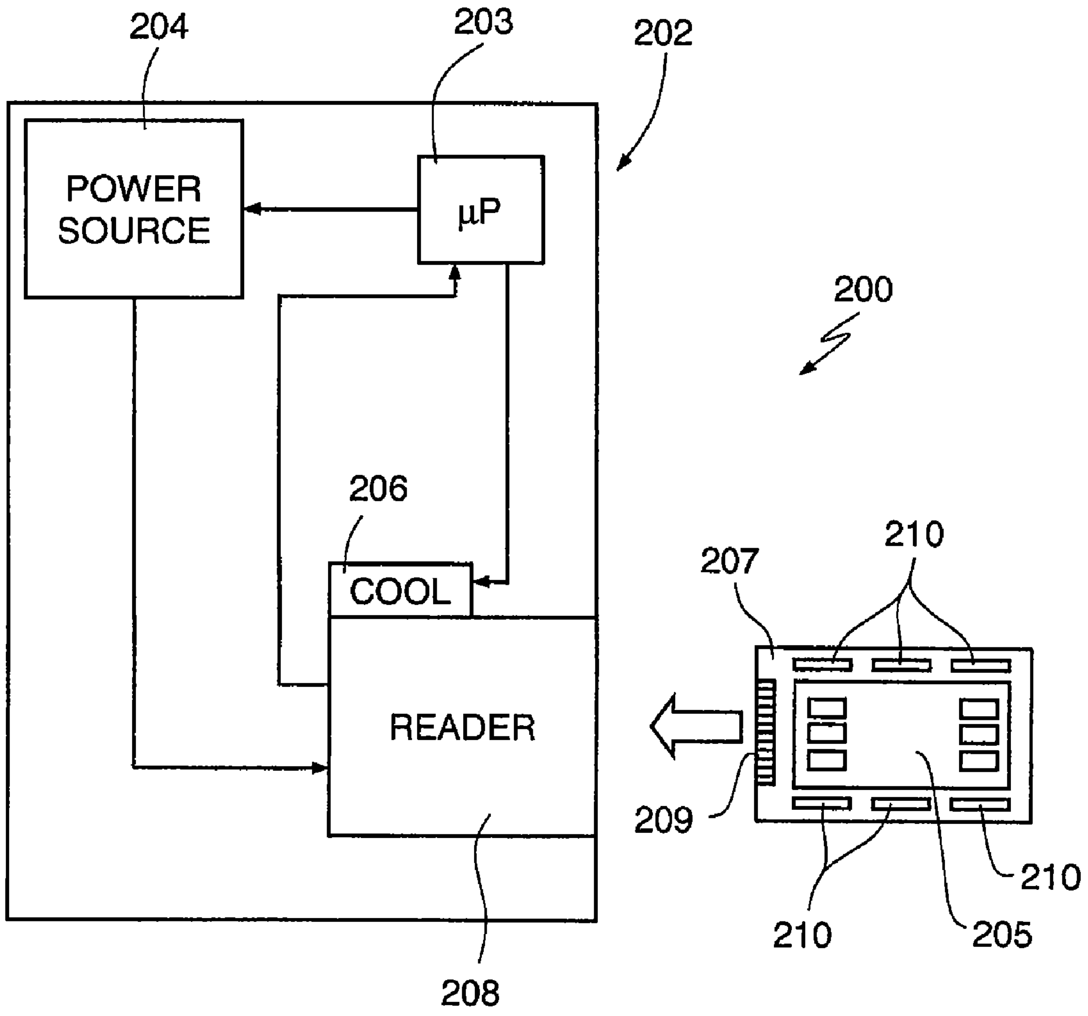
FIG. 8 is a simplified block diagram of an apparatus for performing chemical reactions through a microreactor according to one embodiment of the invention.

With reference to FIG. 8, a biochemical analysis apparatus 200 comprises a computer system 202, including a processing unit 203, a power source 204 controlled by the processing unit 203, and a microreactor chip 205, having the structure and operation already described. The microreactor chip 205 is mounted on a board 207, together making a disposable cartridge which is removably inserted in a reader device 208 of the computer system 202, for selective coupling to the processing unit 203 and to the power source 204. To this end, the board 207 is also provided with an interface 209. Heaters 210 are provided on the board 207 and are coupled to the power source 204 through the interface 209. In another embodiment, heaters are integrated into the reader device 208. The reader device 208 also includes a cooling element 206, e.g. a Peltier module or a fan coil, which is controlled by the processing unit 203 and is thermally coupled to the microreactor 205 when the board 207 is loaded in the reader device 208.

Finally, it is clear that numerous modifications and variations may be made to the device and the method described and illustrated herein, all falling within the scope of the invention, as defined in the attached claims.

What is claimed is:

1. A microreactor for performing chemical reactions, comprising:

a shell structure, having a bottom wall and a peripheral wall;

a layer, accommodated in the shell structure and having one or more cavities formed therein for holding a sample, the cavities being accessible from outside the shell structure;

characterized in that the layer is made of a meltable material that is solid at room temperature, has a melting point ($T_{MP}$) lower than a maximum operative temperature ($T_{MAX}$) required by reactions performable through the microreactor, and wherein the meltable material is immiscible with the sample and water.

2. The microreactor of claim 1, wherein the melting point ($T_{MP}$) is lower than a minimum operative temperature ($T_{MIN}$) required by reactions performable through the microreactor.

3. The microreactor of claim 2, wherein the melting point ($T_{MP}$) is between 50° C. and 70° C.

4. The microreactor of claim 3, wherein the meltable material has a lower specific weight than the sample.

5. The microreactor of claim 1, comprising a cap plate, arranged to close the shell structure, wherein:

the cavities include channels and chambers, fluidly coupled to form a microfluidic circuit defined between the layer and the cap plate; and the cap plate has apertures such that the microfluidic circuit is accessible from outside via the apertures.

6. The microreactor of claim 5, wherein the meltable material has affinity with hydrophobic materials, and the cap plate is hydrophobic.

7. The microreactor of claim 1, comprising a confining structure, formed between the bottom wall and the layer, wherein the confining structure is made of material that has affinity for the meltable material.

8. The microreactor of claim 7, wherein the confining structure is configured to define a window around at least some of the cavities and spots of reagents are arranged on the bottom wall in respective windows.

9. The microreactor of claim 8, wherein the confining structure is made of a hydrophobic material and a surface of the bottom wall is treated to be hydrophilic.

10. The microreactor of claim 1, comprising reagents arranged between the bottom wall and the layer, at locations corresponding to the cavities.

11. A biochemical analysis apparatus comprising a microreactor;

a processing unit;

a power source controlled by the processing unit;

a reader device, for receiving the microreactor and coupling the microreactor to the power source;

wherein the microreactor is made according to claim 1.

12. A method for performing a reaction, comprising:

providing a microreactor including a shell structure and a layer, accommodated in the shell structure and having cavities formed therein for holding a fluid sample, the cavities being accessible from outside the shell structure; and filling the cavities with a fluid sample;

characterized by melting the layer during a reaction and re-solidifying the layer after said reaction, wherein said melting layer is immiscible with said fluid sample and water.

13. The method of claim 12, comprising heating and cooling the microreactor between a maximum operative temperature ($T_{MAX}$) and a minimum operative temperature ($T_{MIN}$), wherein the layer is made of a meltable material that is solid at room temperature, has a melting point ($T_{MP}$), lower than the maximum operative temperature ($T_{MAX}$) and preferably between 50° C. and 70° C.

14. The method of claim 13, wherein the melting point ($T_{MP}$) is lower than the minimum operative temperature ($T_{MIN}$).

15. The method of claim 14, wherein the meltable material has a lower specific weight than water.

16. The method of claim 12, comprising closing the shell structure with a cap plate, provided with apertures for accessing the cavities and treated to be made hydrophobic, wherein the meltable material is hydrophobic.

17. The method of claim 12, comprising providing reagents between a bottom wall of the shell structure and the layer, at locations corresponding to at least some of the cavities.

18. The method of claim 12, comprising:

forming a confining structure, between the bottom wall and the layer;

defining windows in the confining structure around at least some of the cavities; and depositing spots of reagents on the bottom wall in said windows;

wherein the confining structure is made of a hydrophobic material and a surface of the bottom wall inside the windows is treated to be hydrophilic.

* * * * *